US00PP25713P2

(12) United States Plant Patent
Smith

(10) Patent No.: US PP25,713 P2
(45) Date of Patent: Jul. 14, 2015

(54) ***CHRYSANTHEMUM* PLANT NAMED 'CIFZ0025'**

(50) Latin Name: *Chrysanthemum×morifolium*
Varietal Denomination: CIFZ0025

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 79 days.

(21) Appl. No.: 13/998,693

(22) Filed: Nov. 25, 2013

(51) Int. Cl.
*A01H 5/02* (2006.01)

(52) U.S. Cl.
USPC ..... Plt./289

(58) Field of Classification Search
USPC ..... Plt./289
CPC ..... A01H 5/0255; A01H 5/025; A01H 5/02
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0025' particularly distinguished by the medium sized yellow decorative inflorescences, medium plant size with a rounded and mounded habit and a natural flowering response of early October.

1 Drawing Sheet

Latin name of the genus and species of the plant claimed: *Chrysanthemum×morifolium.*

Varietal denomination: 'CIFZ0025'.

BACKGROUND OF THE NEW PLANT

The present invention comprises a new *Chrysanthemum*, botanically known as *Chrysanthemum×morifolium*, and hereinafter referred to by the variety name 'CIFZ0025'.

'CIFZ0025' is a product of a planned breeding program. The new cultivar has medium sized yellow decorative inflorescences, medium plant size with a rounded and mounded habit and a natural flowering response of early October.

'CIFZ0025' originated as a naturally occurring branch mutation found on an unpatented, proprietary seedling identified as 'G0495K4'. 'CIFZ0025' was discovered and selected by the inventor in March 2011 as a flowering branch within a small population of the parent cultivar grown in a pot trial in Gilroy, Calif. The parent cultivar has creamy white colored inflorescences with a plant size that is a bit smaller and a natural season response that is two weeks faster than that of 'CIFZ0025'.

The first act of asexual reproduction of 'CIFZ0025' was accomplished when vegetative cuttings were propagated from the initial selection in April 2011 in a greenhouse in Gilroy, Calif.

BRIEF SUMMARY OF INVENTION

Horticultural examination of plants grown from cuttings of the plant initiated in April 2011, and continuing thereafter, has demonstrated that the combination of characteristics as herein disclosed for 'CIFZ0025' are firmly fixed and are retained through successive generations of asexual reproduction.

'CIFZ0025' has not been observed under all possible environmental conditions. The phenotype may vary significantly with variations in environment such as temperature, light intensity, and day length.

A Plant Breeder's Right for this cultivar was applied for in Canada on Mar. 8, 2013 (13-7959). 'CIFZ0025' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0025' with colors being as true as possible with an illustration of this type.

Figure 1:
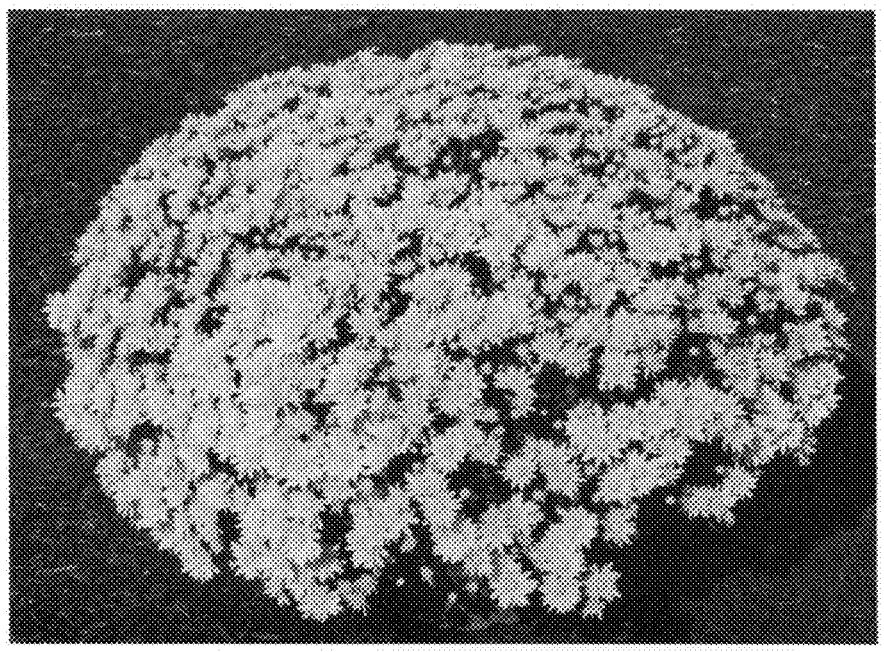
Figure 2:
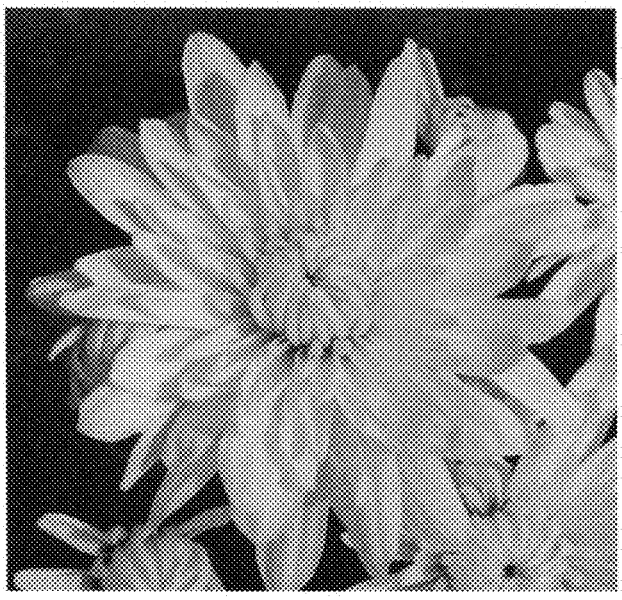

The photographic drawing shows in FIG. 1 a flowering plant of the new variety and in FIG. 2 a close-up of the inflorescences.

DETAILED BOTANICAL DESCRIPTION

The plant descriptions and measurements were taken in Gilroy, Calif. in early September 2013 outdoors in natural light. These plants were grown in 6 inch pots in a greenhouse trial and were about 11 weeks old. These plants were not pinched.

The aforementioned photographs were taken in October 2012 in New Jersey. These plants were about 17-18 weeks of age. They were grown 1 plant per 9 inch pot. These plants were not pinched.

Color references are made to The Royal Horticultural Society Colour Chart (R.H.S.) 2001.

TABLE 1

DIFFERENCES BETWEEN THE NEW VARIETY 'CIFZ0025' AND A MOST SIMILAR VARIETY

| | 'CIFZ0025' | 'Yobethany' (U.S. Plant Pat. No. 16,969) |
|---|---|---|
| Plant size in natural season: | Larger overall | Smaller |
| Plant habit in blackcloth: | Less upright and clubby | More upright and clubby |

TABLE 1-continued

DIFFERENCES BETWEEN THE NEW VARIETY 'CIFZ0025' AND A MOST SIMILAR VARIETY

| | 'CIFZ0025' | 'Yobethany' (U.S. Plant Pat. No. 16,969) |
|---|---|---|
| Inflorescence color: | Bit lighter yellow | Bit darker yellow |
| Inflorescence size: | Larger | Smaller |

Plant:

*Form, growth and habit.*—Herbaceous garden-type, stems upright and somewhat outwardly spreading, freely branching.

*Plant height.*—20-22.0 cm.

*Plant height (inflorescence included).*—24-26.0 cm.

*Plant width.*—44-47.0 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A but lighter.

*Immature, leaf color, lower surface.*—Closest to RHS 137C.

*Mature, leaf color, upper surface.*—Closest to RHS 147A but lighter.

*Mature, leaf color, lower surface.*—Closest to RHS 137C.

*Length.*—4.2-4.9 cm.

*Width.*—2.2-2.4 cm.

*Shape.*—Lanceolate to ovate.

*Base shape.*—Attenuate.

*Apex shape.*—Acute.

*Margin.*—Palmately lobed; slightly irregularly incised; serrate.

*Texture, upper surface.*—Bifid T-shaped hairs.

*Texture, lower surface.*—Bifid T-shaped hairs.

*Color of veins, upper surface.*—Closest to RHS 147B.

*Color of veins, lower surface.*—Closest to RHS 147B.

*Pattern of veining.*—Palmate.

*Petiole color.*—Closest to RHS 147B.

*Length.*—9.0-12.0 cm.

*Diameter.*—0.15 cm.

*Texture.*—Bifid T-shaped hairs.

Stem:

*Quantity of main branches per plant.*—8-10.

*Color of stem.*—Closest to RHS 137B.

*Length of stem.*—14-16.0 cm.

*Diameter.*—0.3 cm.

*Length of internodes.*—0.5-1.0 cm.

*Texture.*—Bifid T-shaped hairs.

*Color of peduncle.*—RHS 137B.

*Length of peduncle.*—3.5-4.0 cm.

*Peduncle diameter.*—0.15 cm.

*Texture.*—Bifid T-shaped hairs.

Inflorescence:

*Type.*—Compositae, solitary decorative-type inflorescences, borne terminally above foliage, ray florets arranged acropetally on a capitulum.

*Quantity of short days to flowering (response time).*—About 8 weeks.

*Natural season flowering.*—Early October.

*Quantity of inflorescences per plant.*—About 50 open with another 50 in immature stages.

*Lastingness of individual blooms on the plant.*—More than 5 weeks from the first color.

*Fragrance.*—Slightly spicy.

Bud (just when opening/showing color):

*Color.*—RHS 6A.

*Length.*—1.1-1.3 cm.

*Width.*—1.2-1.5 cm.

*Shape.*—Broadly oblate.

Immature inflorescence:

*Diameter.*—4-5.5 cm.

*Color of ray florets, upper surface.*—RHS 6A.

*Color of ray florets, lower surface.*—RHS 6B.

Mature inflorescence:

*Diameter.*—About 6.5 cm.

*Depth.*—2.5 cm.

*Total diameter of disc.*—Not showing at this time.

*Receptacle color.*—RHS 144B.

*Receptacle height.*—0.4 cm.

*Receptacle diameter.*—0.4 cm.

Ray florets:

*Average quantity of florets.*—125-130 in several whorls.

*Color of florets, upper surface.*—RHS 6A.

*Lower surface.*—RHS 6B.

*Length.*—2.2-2.5 cm.

*Width.*—0.6-0.8 cm.

*Shape.*—Oblong.

*Apex shape.*—Rounded.

*Base shape.*—Cuneate.

*Margin.*—Entire.

*Texture, upper surface.*—Papillose.

*Texture, lower surface.*—Papillose.

Disc florets:

*Average quantity of florets.*—9-15.

*Color of florets.*—RHS 1C but a little lighter.

*Length.*—0.2 cm.

*Width.*—0.1 cm.

*Shape.*—Tubular, elongated.

*Apex shape.*—Acute, 5 pointed.

*Texture, inner surface.*—Glabrous.

*Texture, outer surface.*—Glabrous.

Phyllaries:

*Quantity.*—About 20.

*Color, upper surface.*—Closest to RHS 137A.

*Color, lower surface.*—Closest to RHS 137A.

*Length.*—0.5-0.7 cm.

*Width.*—0.2 cm.

*Shape.*—Lanceolate.

*Apex shape.*—Acute.

*Base.*—Cuneate.

*Margins.*—Entire.

*Texture, upper surface.*—Glabrous.

*Texture, lower surface.*—Bifid T-shaped hairs.

Reproductive organs:

*Pistil.*—1, found on both types of florets.

*Length.*—0.4-0.5 cm.

*Style color.*—RHS 1B.

*Style length.*—0.3-0.4 cm.

*Stigma color.*—RHS 6B.

*Stigma shape.*—Bi-parted.

*Ovary color.*—RHS 144B.

*Ovary length.*—0.1 cm.
*Ovary width.*—0.1 cm.
*Stamens.*—4, found only on the disc florets.
*Color of filaments.*—RHS 1C.
*Length filaments.*—0.175 cm.
*Anther color.*—RHS 15B.
*Anther length.*—0.1 cm.
*Anther shape.*—Oblong.
*Color of pollen.*—RHS 15A.
*Pollen amount.*—Sparse.
*Fertility/seed set.*—Has not been determined to date.
Disease/pest resistance: Has not been determined to date.

What is claimed is:

1. A new and distinct variety of *Chrysanthemum* plant named 'CIFZ0025' substantially as illustrated and described herein.

* * * * *